United States Patent [19]

Chung

[11] 4,328,161

[45] May 4, 1982

[54] PROCESS FOR THE PREPARATION OF 1-AMINOANTHRAQUINONES

[75] Inventor: Rack H. Chung, Clifton Park, N.Y.

[73] Assignee: BASF Wyandotte Corporation, Wyandotte, Mich.

[21] Appl. No.: 834,993

[22] Filed: Sep. 20, 1977

[51] Int. Cl.$^3$ .................. C07C 97/24; C07C 97/26; C07C 143/665
[52] U.S. Cl. ............................ 260/378; 260/384; 260/371; 260/373; 260/380; 260/381
[58] Field of Search ............... 260/369, 384, 376, 522, 260/378, 371, 373, 380, 381

[56] References Cited

U.S. PATENT DOCUMENTS

| | | | |
|---|---|---|---|
| 1,551,373 | 8/1925 | Daudt | 260/522 |
| 1,966,067 | 7/1934 | Jaeger | 260/522 |
| 2,499,003 | 1/1950 | Scalera | 260/376 |
| 2,659,738 | 11/1953 | Schlichting et al. | 260/376 |
| 3,978,096 | 8/1976 | Eilingsfeld et al. | 260/384 |

FOREIGN PATENT DOCUMENTS

| | | | |
|---|---|---|---|
| 678608 | 9/1952 | United Kingdom | 260/376 |
| 172839 | 8/1965 | U.S.S.R. | 260/376 |
| 197050 | 7/1967 | U.S.S.R. | 260/376 |

OTHER PUBLICATIONS

*Methoden der Organischen Chemie*, Houben-Weyl vol. 8, pp. 484–496.

*Journal of the Society of Dyers & Colorists*, vol. 66, pp. 229–231, Apr. 1950 "Aromatic Nitro Compounds" Hodgson, Heyworth & Word.

*Chemical Abstracts*, vol. 71, 1969 Abstract No. 48900m, Long, "Mechanisms for Decarboxylation of Aromatic Acids".

*Chemical Abstracts*, vol. 74, 1974 Abstract No. 52664s, p. 268, Manikyam "Thermal decarboxylation of Benzoic Acids".

*Chemical Abstracts* vol. 74, 1971 Abstract No. 640020s, p. 287 Chodowska–Palicka, "Decarboxylation of 2-Nitro Benzoic Acids".

*Chemical Abstracts*, vol. 67, 1967 Abstract No. 43191n, p. 4036 Rekkev et al. "Decarboxylation of substituted 4–Aminobenzoic Acid in Aqueous Solution".

*Chemical Abstracts*, vol. 85, 1976 Abstract, No. 177120v, p. 495, Morley "Synthesis of Aminoanthraquinones by Sodium Borohydride Reduction of Nitroanthraguinones".

*Chemical Abstracts*, vol. 81, 1974, abstract No. 27, 207q; Schuhmacher, A. Kohlhaupt, R; Hiller, H. "1-Nitro-2-anthraquinone carboxylic acid".

*Chemical Abstracts*, vol. 85, 1976, p. 495, Abstract No. 177,124z; Morley O., "Synthesis of Aminoanthraquinone by Sodium Borohydride Reductions of Nitroanthraquinones".

*Primary Examiner*—Winston A. Douglas
*Assistant Examiner*—Raymond Covington
*Attorney, Agent, or Firm*—Joseph D. Michaels; Samson B. Leavitt

[57] ABSTRACT

A selective process for the preparation of 1-aminoanthraquinones from the corresponding 1-aminoanthraquinone-2-carboxylic acid by decarboxylation in an acid solution in the presence of iron or zinc as a catalyst.

11 Claims, No Drawings

PROCESS FOR THE PREPARATION OF 1-AMINOANTHRAQUINONES

The present invention provides a simplified and efficient process for selectively producing 1-aminoanthraquinones in a substantially pure state and in high yield.

The 1-aminoanthraquinone is an important intermediate in the manufacture of a wide variety of dyestuffs, pharmaceuticals, thickening agents, etc., being used either as such or after conversion to a corresponding derivative. Specifically, 1-aminoanthraquinone is used in the manufacture of bromamine acid and 1-amino-2-bromo-4-hydroxyanthraquinone from which Genacron Cerise N and Genacron Cerise NSL and other valuable dyestuffs are produced.

Typical reactions for the 1-aminoanthraquinone isomer are treatment with concentrated oleum or chlorosulfonic acid to form the 1-amino-2-sulfonic acid derivative followed by treatment with bromine to form bromamine (1-amino-4-bromo-anthraquinone-2-sulfonic acid), or the 1-aminoanthraquinone compound can be dibrominated to form 2,4-dibromo-1-amino-anthraquinone, which, in turn can be hydrolyzed with concentrated sulfuric and boric acids to provide 1-amino-2-bromo-4-hydroxyanthraquinone. The 1-aminoanthraquinone can also be treated with chloroform to give the isocyanide derivative and reaction with nitrous acid gives the corresponding diazonium salt which, in turn, is hydrolyzed to the hydroxy derivative.

In the past, 1-aminoanthraquinone has been prepared by treatment of anthraquinone with oleum in the presence of mercury to produce anthraquinone-1-sulfonic acid which, in turn, is reacted with ammonia in the presence of arsenic. Since the present process does not require mercury or arsenic, it avoids serious pollution problems associated with their use and disposal.

Further disadvantages of prior processes using mercury and arsenic appear to be due to the fact that traces of these elements can be found in the final product, which are prohibitive in the preparation of pharmaceuticals.

Accordingly, it is an object of the present invention to provide a commercially feasible and economical process for the selective production of 1-aminoanthraquinone and substituted derivatives thereof.

It is another object of the present invention to provide a process for the production of 1-aminoanthraquinone in high yield and in a substantially pure state, e.g. above about 95%.

These and other objects of the present invention will become apparent from the following description and disclosure.

In accordance with the present invention, a 1-aminoanthraquinone-2-carboxylic acid having the formula:

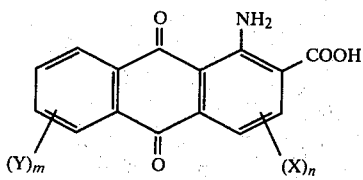

where X is hydroxy, alkoxy of from 1 to 4 carbon atoms, halo, amino or —SO$_3$H; Y is hydroxy, alkoxy of from 1 to 4 atoms, halo, amino or —SO$_3$H; and m and n independently represent a value of from 0 to 2, is dissolved in an aqueous carboxylic acid or suspended in mineral acid solution and decarboxylated in the presence of iron, tin or zinc in particulate form, at a temperature of from about 50° C. to about 150° C. under from about 5 to about 100 psig, preferably at a temperature of from about 80° C. to about 110° C. or reflux under atmospheric pressure.

The aqueous carboxylic acid solution of 1-aminoanthraquinone-2-carboxylic acid is preferably prepared by dissolving said 1-aminoanthraquinone-2-carboxylic acid in a 50–90% aqueous solution of an unsubstituted carboxylic acid having from 1 to 4 carbon atoms, preferably formic or acetic acid. The aqueous mineral acid dispersion of 1-aminoanthraquinone-2-carboxylic acid is preferably prepared by suspending said 1-aminoanthraquinone-2-carboxylic acid in a 20–50% aqueous solution of the mineral acid, preferably H$_2$SO$_4$ or HCl. The moles of said C$_1$ to C$_4$ acid or mineral acid employed may vary between about 4 and about 10, and is preferably between about 4 and about 8 moles per mole of 1-aminoanthraquinone-2-carboxylic acid. To this solution is added from about 0.1 mole to about 0.5 moles, more desirably between about 0.2 moles and about 0.4 moles, of the metal catalyst per mole of 1-aminoanthraquinone-2-carboxylic acid. The mixture is then reacted at elevated temperature, preferably by refluxing for a period of from about 0.5 to about 8 hours, more desirably from about 0.5 to about 5 hours, during which time carbon dioxide gas is generated. The carbon dioxide by-product can be vented to the atmosphere or the reaction can be conducted in a closed system wherein the generation of carbon dioxide gradually increases the pressure and the reaction is run under autogenous conditions. If desired, the reaction can be run under a blanket of nitrogen gas; although such operation under nitrogen is not necessary to achieve the benefits of the present invention. A pH of between about 4 and about 6 is maintained during reaction.

After the reaction is completed as noted by constant pressure or cessation of carbon dioxide generation, the reaction mixture containing product is drowned in water to precipitate the 1-aminoanthraquinone which is then filtered from the reaction mixture and water washed until free of acid and dried to selectively produce 1-aminoanthraquinone. The product may be recrystallized from glacial acetic acid if desired, but is directly obtained in sufficient purity for immediate use without further purification.

If desired, after drowning the reaction mixture in water, e.g. with between about 0.5 and about 5 volumes of water per volume of mixture, and before filtration of product, the diluted reaction mixture can be digested over a steam bath for a period of up to 2 hours. Such digestion over steam enhances subsequent filtration by forming more discrete particles of the product.

By the process of the present invention, the 1-aminoanthraquinone product is recovered in at least 70% yield and in a substantially pure state. This product is suitable for further reaction without additional purification; thus, the 1-aminoanthraquinone obtained in this manner can be directly used as a valuable coupling agent or converted to other dyestuff intermediates, such as, 1-amino-4-bromoanthraquinone-2-suffonic acid or 1-amino-2-bromo-4-hydroxyanthraquinone.

The 1-aminoanthraquinone-2-carboxylic acid starting materials of the present process are prepared by the general process of the following equation:

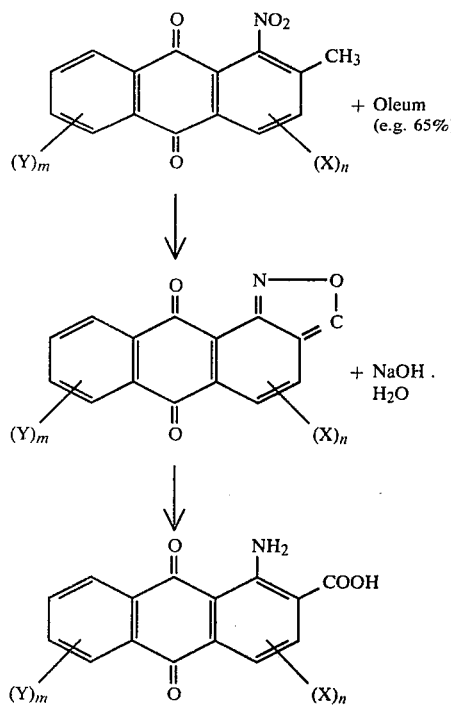

wherein X, Y, m and n are as defined above. This reaction, after the addition of oleum, is effected at a temperature between about −5° C. and about 10° C. under atmospheric pressure.

Having generally described the present invention, reference is now had to the accompanying examples which illustrate preferred embodiments, but which are not to be construed as limiting to the scope of the present invention as set forth in the foregoing disclosure and in the appended claims. All amounts and proportions recited in the following examples are by weight unless otherwise indicated. It is also to be understood that any of the substituted 1-aminoanthraquinone-2-carboxylic acids can replace 1-aminoanthraquinone-2-carboxylic acid in the following examples to provide the corresponding, decarboxylated product.

EXAMPLE 1

1-Nitro-2-methylanthraquinone (30 g 0.11 mole) was added to 125 ml. of 65% oleum in portions sufficient to maintain the temperature below 5° C. The temperature at 5° C. is assisted by means of an ice-salt bath. After the addition was complete the mixture was stirred for 15 minutes at the same temperature. The reaction mixture was then poured slowly over ice. The dark brownish-yellow solid which formed was collected by filtration and washed with water. The wet cake was heated with 1130 ml. of 10% sodium hydroxide solution for one hour at 100° C. After being cooled to room temperature, the mixture was acidified with 6 N hydrochloric acid. The solid 1-aminoanthraquinone-2-carboxylic acid which precipitated was collected by filtration and washed with water and dried.

To a three-necked round-bottomed flask equipped with stirrer and reflux condenser was added 5 g (0.014 mole) 1-aminoanthraquinone-2-carboxylic acid, 1 g (0.0037 mole) zinc powder, and 40 ml of 90% acetic acid. The mixture was refluxed gently for 4 hours during which time carbon dioxide was evolved. The reaction mixture was then poured into 200 ml of water and the resulting mixture was heated on a steam bath for 30 minutes. The red solid which precipitated was collected by filtration and washed with water to give 3.5 g (82% yield) of more than 90% pure 1-aminoanthraquinone.

EXAMPLE 2

Example 1 was repeated using 0.2 g (0.0037 mole) of iron powder in place of zinc powder. A similar yield and product purity was obtained.

EXAMPLE 3

Example 1 was repeated using 1.9 q (0.007 mole) of 1-amino-4-hydroxyanthraquinone-2-carboxylic acid instead of 1-aminoanthraquinone-2-carboxylic acid. A good yield of substantially pure 1-amino-4-hydroxyanthraquinone was obtained.

EXAMPLE 4

Example 1 was repeated using 2.3 g (0.007 mole) of 1-amino-4-bromoanthraquinone-2-carboxylic acid instead of 1-aminoanthraquinone-2-carboxylic acid. A good yield of substantially pure 1-amino-4-bromoanthraquinone was obtained.

What is claimed is:

1. A process for selectively producing a 1-aminoanthraquinone which comprises:
   (a) forming an acid aqueous medium of a $C_1$ to $C_4$ carboxylic acid or a mineral acid and a 1-aminoanthraquinone-2-carboxylic acid having the formula:

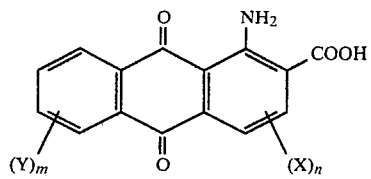

wherein X is hydroxy, alkoxy of from 1 to 4 carbon atoms, halo, amino or $-SO_3H$; Y is hydroxy, alkoxy of from 1 to 4 carbon atoms, halo, amino or $-SO_3H$; and m and n independently represent a value of from 0 to 2;
   (b) contacting the resulting acid medium from (a) with between about 0.1 mole and about 0.5 moles of elemental iron, tin or zinc metal as the catalyst, per mole of 1-aminoanthraquinone-2-carboxylic acid at an elevated temperature to effect decarboxylation; and
   (c) recovering the corresponding product of the process having formula:

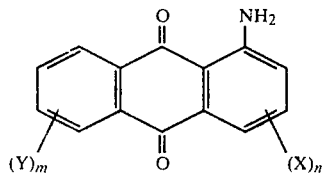

wherein the substituents X and Y and subscripts m and n are the same as defined above.

2. The process of claim 1 wherein a 20–50% aqueous mineral acid solution is employed to form the acid medium.

3. The process of claim 1 wherein a 50–90% aqueous $C_1$ to $C_4$ carboxylic acid solution is employed to form the acid solution.

4. The process of claim 1 wherein the decarboxylation is effected at between about 50° C. and about 150° C. under from about 5 psig to about 100 psig.

5. The process of claim 1 wherein the metal employed is zinc.

6. The process of claim 1 wherein the metal employed is iron.

7. The process of claim 1 wherein the 1-aminoanthraquinone-2-carboxylic acid is unsubstituted as when m and n are 0.

8. The process of claim 1 wherein the reaction mixture from step (b) is digested over steam for a period of up to 2 hours and the digested mixture is filtered to recover the 1-aminoanthraquinone product of the process.

9. The process of claim 1 wherein the reaction is conducted at a pH of from about 4 to about 6.

10. The process of claim 3 wherein the acid is acetic acid.

11. The process of claim 1 wherein the metal employed is tin.

* * * * *